(12) United States Patent
Scheller et al.

(10) Patent No.: US 7,473,249 B2
(45) Date of Patent: *Jan. 6, 2009

(54) DIRECTIONAL LASER PROBE

(75) Inventors: Gregg D. Scheller, Wildwood, MO (US); Michael D. Auld, Chesterfield, MO (US)

(73) Assignee: Synergetics, Inc., O'Fallon, MO (US)

( * ) Notice: Subject to any disclaimer, the term of this patent is extended or adjusted under 35 U.S.C. 154(b) by 121 days.

This patent is subject to a terminal disclaimer.

(21) Appl. No.: 11/328,515

(22) Filed: Jan. 9, 2006

(65) Prior Publication Data

US 2006/0173448 A1    Aug. 3, 2006

Related U.S. Application Data

(62) Division of application No. 10/409,874, filed on Apr. 9, 2003, now Pat. No. 6,984,230.

(51) Int. Cl.
*A61B 18/18* (2006.01)

(52) U.S. Cl. .................. 606/15; 606/4; 607/89

(58) Field of Classification Search .......... 606/2, 606/2.5, 4–7, 13–16, 18; 607/88, 89
See application file for complete search history.

(56) References Cited

U.S. PATENT DOCUMENTS

| | | | |
|---|---|---|---|
| 4,347,837 A | 9/1982 | Hosono | |
| 4,674,497 A | 6/1987 | Ogasawara | |
| 4,744,360 A | 5/1988 | Bath | |
| 5,156,604 A | 10/1992 | Hessel et al. | |
| 5,172,685 A | 12/1992 | Nudelman | |
| 5,281,214 A * | 1/1994 | Wilkins et al. | ............. 606/15 |
| 5,300,061 A | 4/1994 | Easley et al. | |
| 5,372,585 A | 12/1994 | Tiefenbrun et al. | |
| 5,469,524 A | 11/1995 | Esch et al. | |
| 5,512,034 A | 4/1996 | Finn et al. | |
| 5,520,222 A | 5/1996 | Chikama | |
| 5,603,710 A | 2/1997 | Easley et al. | |
| 5,656,011 A | 8/1997 | Uihlein et al. | |
| 5,688,264 A | 11/1997 | Ren et al. | |
| 5,735,792 A | 4/1998 | Vanden Hoek et al. | |
| 5,741,225 A | 4/1998 | Lax et al. | |
| 5,766,164 A | 6/1998 | Mueller et al. | |
| 5,807,242 A | 9/1998 | Scheller et al. | |
| 5,855,577 A * | 1/1999 | Murphy-Chutorian et al. | . 606/7 |
| 5,865,831 A | 2/1999 | Cozean et al. | |
| 5,957,916 A | 9/1999 | Jeevanandam et al. | |
| 5,993,072 A | 11/1999 | de Juan, Jr. et al. | |
| RE36,473 E * | 12/1999 | Esch et al. | .............. 385/118 |
| 6,015,403 A | 1/2000 | Jones | |
| 6,053,911 A | 4/2000 | Ryan et al. | |
| 6,129,721 A | 10/2000 | Kataoka et al. | |

(Continued)

FOREIGN PATENT DOCUMENTS

WO    WO 95/31926    11/1995

(Continued)

*Primary Examiner*—A. Farah
(74) *Attorney, Agent, or Firm*—Thompson Coburn LLP

(57) ABSTRACT

A microsurgical laser probe is provided with a distal end portion of an optic fiber that projects from a tubular sleeve of the probe and can be caused to bend relative to the probe sleeve by manual manipulation of a mechanism on a handle of the probe.

26 Claims, 3 Drawing Sheets

U.S. PATENT DOCUMENTS

| | | |
|---|---|---|
| 6,142,990 A | 11/2000 | Burk |
| 6,428,553 B1 | 8/2002 | Trese |
| 6,572,608 B1 * | 6/2003 | Lee et al. .................. 606/15 |
| 6,575,989 B1 | 6/2003 | Scheller et al. |
| 6,984,230 B2 * | 1/2006 | Scheller et al. ............ 606/15 |
| 7,141,048 B1 | 11/2006 | Charles |
| 2005/0154379 A1 * | 7/2005 | McGowan et al. .......... 606/4 |
| 2006/0004348 A1 * | 1/2006 | Scheller et al. ............ 606/4 |

FOREIGN PATENT DOCUMENTS

WO     WO96/41578     12/1996

* cited by examiner

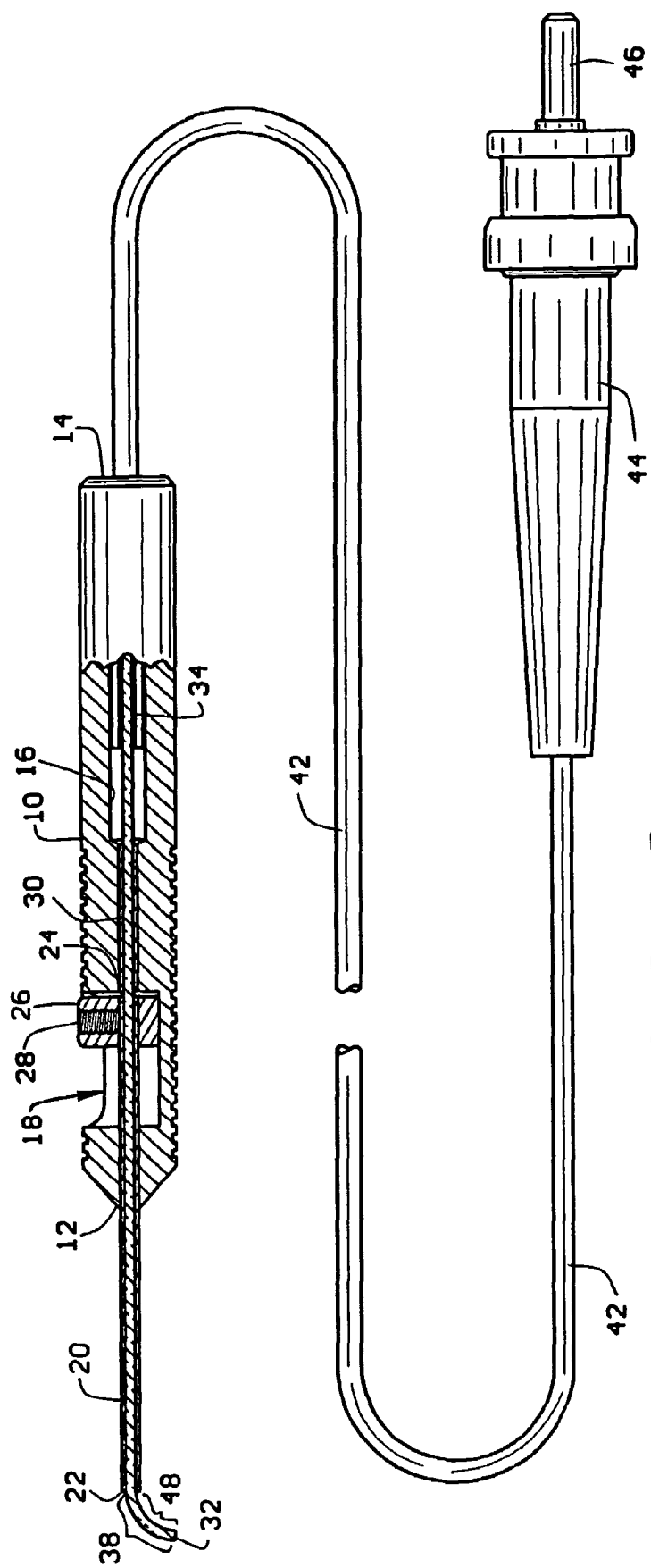
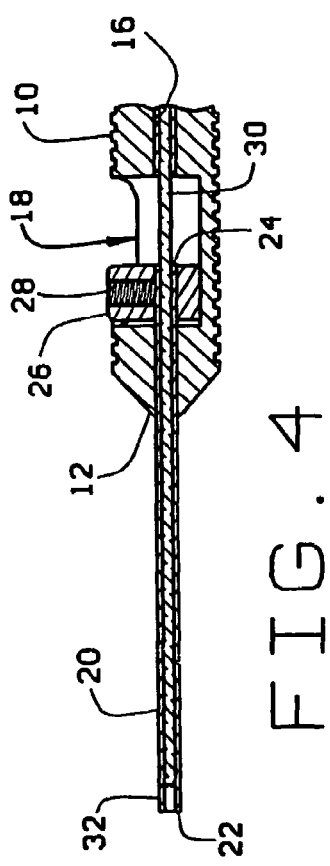
FIG. 3
FIG. 4

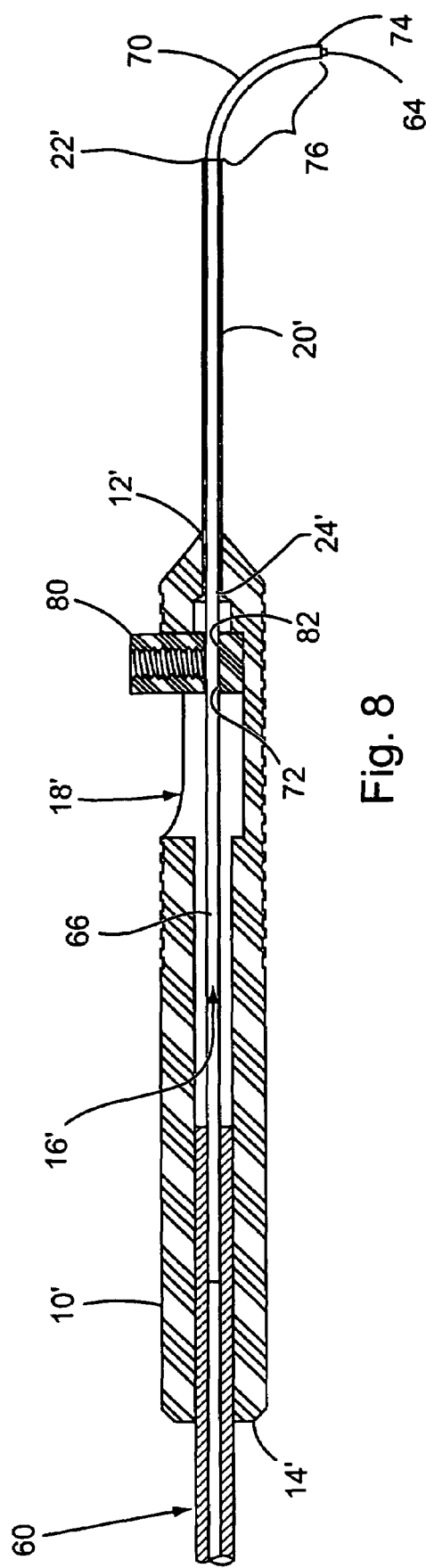
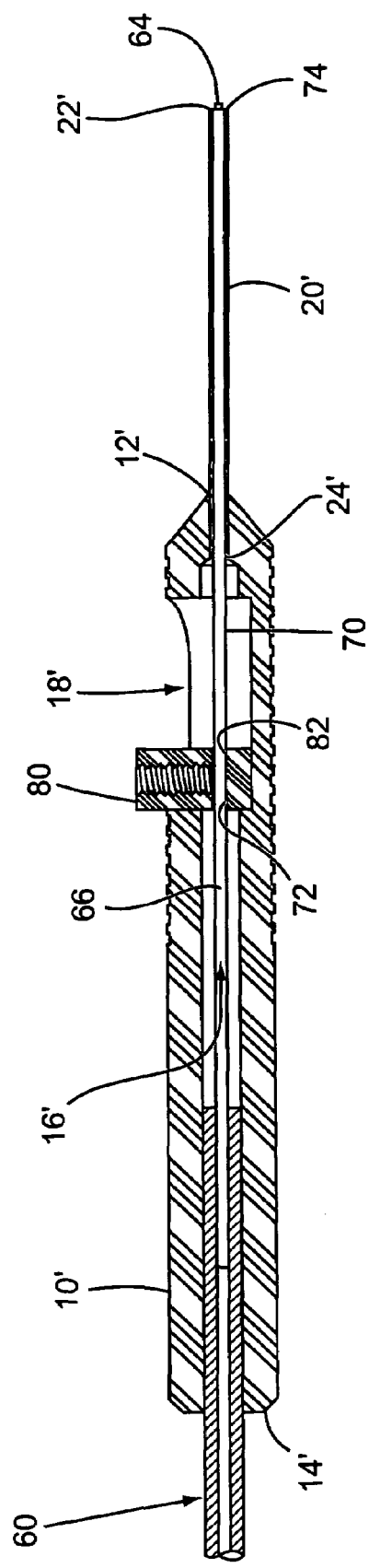

DIRECTIONAL LASER PROBE

This application is a divisional of patent application Ser. No. 10/409,874, which was filed on Apr. 9, 2003, and which issued as U.S. Pat. No. 6,984,230 B2 on Jan. 10, 2006.

BACKGROUND OF THE INVENTION (1) Field of the Invention

The present invention pertains to a microsurgical laser probe used primarily in ophthalmic surgery. The probe has a handle and a tubular sleeve and a distal end portion of an optic fiber projecting from the sleeve can be caused to bend relative to the sleeve by manual manipulation of a mechanism on the probe handle.

(2) Description of the Prior Art

In ophthalmic surgery, various different types of instruments are available for use by the surgeon to transmit laser energy to a surgical site in the interior of the eye. The typical microsurgical laser probe comprises a handle with a small cylindrical metal sleeve projecting from a distal end of the handle. An optic fiber, having a proximal end with a connector for coupling to a source of laser light, passes through the center of the handle and the sleeve of the probe. The distal end of the optic fiber is positioned adjacent the distal end of the sleeve. In instruments of this type, the sleeve can project straight from the handle of the instrument or can have a slight bend or curve as it projects from the instrument handle.

Efficient delivery of laser light in the eye interior toward the anterior or front portion of the retina is often awkward to the surgeon using a straight laser probe. This is due to the positioning of the incision or instrument entry site in the eye relative to the target area or surgical site of the laser light being transmitted. This is illustrated in FIG. 1 where an area A of the eye interior is inaccessible to the straight tip of the laser probe shown. The use of curved laser probes such as that shown in FIG. 2 allows for a greater range of coverage inside the eye, thereby minimizing the risk of hitting the lens of the eye with the laser light and overcoming the disadvantages of the straight sleeve laser probe discussed above. However, curved laser probes cannot be inserted through straight cannulas and therefore must be directed through the eye incision site itself.

The optimal deliver of laser light to a surgical site in the eye requires that the laser be directed perpendicular to the target area of the surgical site. Directing a straight laser probe at anterior or forward portions of the retina causes the approach angle, or angle of incidence of the laser light, to be large. In this situation the optimal delivery of laser light to the surgical site cannot be achieved. Additionally, torquing or manipulating the tubular sleeve of the straight probe in the entry incision to reduce the angle of approach of the laser light to the surgical site in these awkward areas often produces excessive, and sometimes harmful stresses around the incision of the eye. Often the only way for the surgeon to overcome this situation is to create a second incision site for insertion of the laser probe. These problems can be overcome by using a curved laser probe that can effectively eliminate the use of a secondary incision site since an increased area in the eye interior is accessible from the single entry site as illustrated in FIG. 2. Currently available curved laser probes are able to access more anterior or forward areas of the eye interior than can be achieved with straight laser probes. However, because their curvatures are fixed, curved laser probes are not efficient at directing laser energy to areas even more anterior or more forward in the eye that would require a tighter bend or curvature of the probe sleeve, or areas at the far end or posterior of the retina which would require a straight sleeve laser probe due to the approach angle.

To overcome these disadvantages of prior art straight and curved laser probes, what is needed is an adjustable directional laser probe that is capable of reducing the approach angle or angle of incidence of light toward the surgical site, thereby providing ease of access and reduced instrument manipulation at the target site, reduced tissue stress at the point of entry, and improved laser focusing by directing the laser energy more perpendicular to the target surgical site.

SUMMARY OF THE INVENTION

The directional laser probe of the present invention may be constructed having either a disposable hand piece or a reusable hand piece and, although described as transmitting laser light, it may also be employed in transmitting light for illumination. The directional laser probe makes use of a shape memory metal alloy, nitinol, to steer and direct a flexible optic fiber to a surgical target site. Alternative shape memory materials such as spring steel or plastics may also be used. Whether the target site lies in the posterior or anterior portions of the eye interior, the directional laser probe can easily deflect to any angle between 0° (or a straight configuration) and 90° or more. The flexible nature of the shape memory material allows variable adjustment of the bend angle of the probe to deliver laser energy to the target site. Additionally, cannulas may be used in the incision site of the eye because the laser probe, when in its straight configuration, can be inserted through the cannula to position the tip of the probe in the interior of the eye, and then a bend can be created at the tip of the probe in the eye interior. The directional laser probe is especially useful when accessing anterior portions of the retina, or areas that are difficult or awkward to access using traditional straight probes.

The directional laser probe of the invention is basically comprised of a handle having an interior bore passing through its center and having a recess formed in a side of the handle communicating with the interior bore. A tubular sleeve projects from a distal end of the handle, and is received in the bore for axial sliding movement relative to the handle. A finger pad positioned in the recess is connected to the sleeve and manipulating the finger pad axially through the recess causes the sleeve to be moved between a pushed forward position where it projects its greatest distance from the distal end of the handle, and a pulled back position where the sleeve projects its shortest distance from the distal end of the handle. A tubular tip of shape memory material passes through the sleeve and is secured stationary relative to the handle. A length of optic fiber enters the handle bore at the handle proximal end and a distal end portion of the optic fiber passes through the bore and the shape memory tip. The proximal end of the fiber is connected to a standard light source connector, for example a SMA type connector.

The shape memory tip that passes through the sleeve is initially set in a pre-bent 90° bend in a preferred embodiment. When the finger pad of the instrument is pushed forward, it extends the sleeve to its pushed forward position in which the shape memory tip and the distal end portion of the optic fiber are completely contained inside the tubular sleeve. When the finger pad is moved to its pulled back position, the sleeve is also moved back to its pulled back position causing the bent portion of the shape memory tip and the distal end portion of the optic fiber to be gradually exposed at the distal end of the sleeve. As the shape memory tip and the optic fiber contained therein are exposed at the end of the sleeve, they gradually bend from the initial straight configuration of the sleeve toward the 90° pre-bent configuration of the shape memory tip. In this manner, the optic fiber contained in the shape memory tip can be adjustably positioned through any angle between 0° when the shape memory tip and optic fiber are entirely contained in the tubular sleeve at its pushed forward position, to a 90° bend when the shape memory tip and optic fiber project from the sleeve distal end with the sleeve moved to its pulled back position.

In a second embodiment of the directional probe the sleeve is secured stationary to the handle and the optic fiber reciprocates through the handle and the sleeve. A tubular pre-bent tip is secured to a distal end portion of the optic fiber and slides through the sleeve on reciprocating movement of the optic fiber. The finger pad is connected to the pre-bent tip and the portion of the optic fiber therein.

In use of both embodiments of the directional laser probe, the optic fiber connector is first attached to a laser power source. In the first embodiment of the probe where the sleeve is moveable, with the finger pad initially in its pushed forward position, the optic fiber is contained in the sleeve which projects in a straight line from the distal end of the handle. In the second embodiment of the probe where the optic fiber is moveable, with the finger pad initially in its pulled back position, the optic fiber is contained in the sleeve.

In use of both embodiments the sleeve is then inserted through a cannula positioned in an incision in the eye or the sleeve is inserted directly through the incision, positioning the sleeve in the eye interior. In the first embodiment, the finger pad is then slowly moved toward the rear of the handle causing the sleeve to slowly move toward its pulled back position relative to the handle. In the second embodiment, the finger pad is moved slowly toward the front of the handle causing the optic fiber to slowly move toward its pushed forward position relative to the handle. In both embodiments the distal end portion of the optic fiber contained in the pre-bent portion of the tubular shape memory tip gradually bends from its straight configuration toward its 90° configuration. The bending of the fiber allows optimal positioning of the fiber tip to areas where a straight fiber may not reach. Rotation of the entire instrument about its center axis may be necessary to further direct the optic fiber tip. Once the proper location of the fiber tip is achieved, laser energy can then be delivered to the site of interest. Retraction of the optic fiber tip into the sleeve of the first embodiment is performed by pushing the finger pad forward, causing the sleeve to move toward its pushed forward position and causing straightening of the bent portion of the optic fiber projecting from the sleeve. Retraction of the optic fiber into the sleeve of the second embodiment is performed by pulling the finger pad rearward, causing the bent portion of the optic fiber to be pulled back into the sleeve. With the optic fiber contained in the sleeve, the sleeve is then pulled back through the surgical entry site.

DESCRIPTION OF THE DRAWINGS

Further objects and features of the present invention will be revealed in the following detailed description of the preferred embodiment of the invention and in the drawing figures, wherein:

FIG. 3 is a partially sectioned view of the directional laser probe of the first embodiment of the invention with the curved optic fiber projecting from the probe sleeve;

FIG. 4 is a partial sectioned view of the instrument sleeve with the optic fiber in its straight configuration;

FIG. 8 is a sectioned view of the directional laser probe of the second embodiment of the invention with the curved optic fiber projecting from the probe sleeve; and, FIG. 9 is a partial sectioned view of the directional laser probe of FIG. 8 with the optic fiber in its straight configuration.

DETAILED DESCRIPTION OF THE PREFERRED EMBODIMENT

Figure 1:
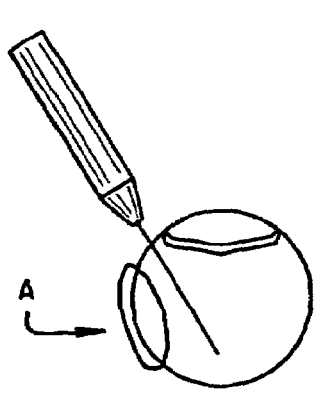
FIG. 1 is an illustration of a conventional straight laser probe employed in ophthalmic surgery.
Figure 2:
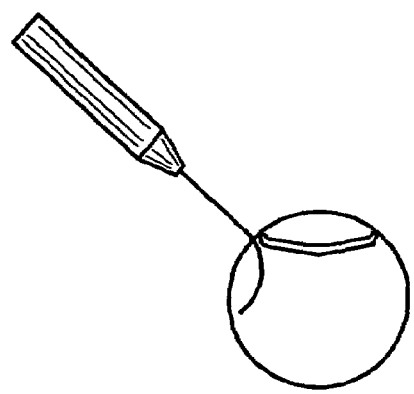
FIG. 2 is a view similar to FIG. 1 but showing a conventional curved laser probe.

The directional laser probe of the invention is described herein as transmitting laser light for use in laser surgery of the eye. However, the probe is equally well suited for use in transmitting light for illumination. In addition, the probe can be designed as a disposable instrument or as a reusable instrument.

The directional laser probe is provided with an elongated narrow handle or hand piece 10 having opposite distal 12 and proximal 14 ends. The handle 10 is dimensioned to a size similar to that of a pencil to fit comfortably in the surgeon's hand. The handle is preferably manufactured of a disposable medical grade plastic. A hollow bore 16 extends through the center of the handle from its distal end 12 to its proximal end 14. The bore 16 enlarges slightly adjacent the proximal end 14 of the handle. A recess 18 is formed into a side of the handle and intersects the center bore 16. The recess 18 extends axially along a short length of the handle forming an axial slot.

A cylindrical narrow tube or sleeve 20 of stainless steel is received in the bore 16 at the distal end 12 of the handle for sliding movement of the sleeve 20 through the bore. The sleeve 20 projects from the handle distal end 12 to a distal end 22 of the sleeve. The opposite proximal end 24 of the sleeve is positioned in the recess or slot 18 of the handle.

A finger pad 26 is positioned in the slot 18 for axial sliding movement of the finger pad through the slot between a pushed forward position of the finger pad 26 shown in FIG. 4 and a pulled back position of the finger pad shown in FIG. 3. The finger pad 26 is preferably constructed of disposable medical grade plastic. The finger pad has a hole into which the sleeve proximal end 24 is inserted. A set screw 28 secures the finger pad 26 to the proximal end 24 of the sleeve. Thus, moving the finger pad 26 to its pushed forward position shown in FIG. 4 will also move the sleeve 20 through the handle bore 16 to its forward most position or pushed forward position relative to the handle 10 where it projects its greatest distance from the handle distal end 12. Moving the finger pad 26 to its pulled back position shown in FIG. 3 will also move the sleeve 20 to its pulled back position relative to the handle 10 where the sleeve distal end 22 projects its shortest distance from the handle distal end 12. In the preferred embodiment of the invention, the travel distance of the finger pad 26 in the slot 18 and of the sleeve distal end 22 is 25 mm.

Figure 5:
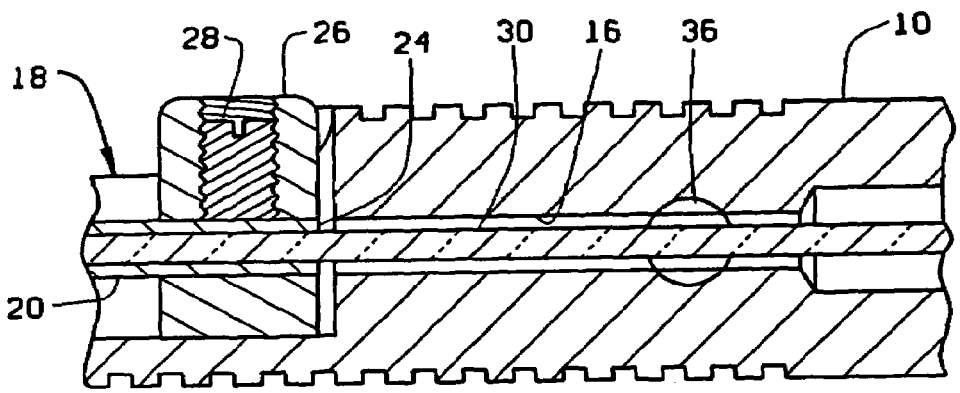
FIG. 5 is a partial sectioned view showing the connections of the sleeve and optic fiber in the instrument handle.
Figure 6:
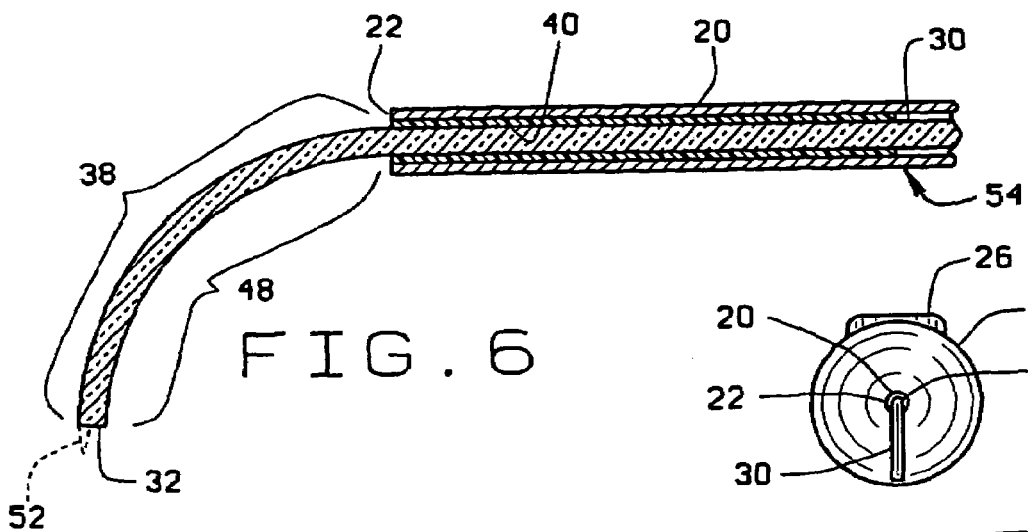
FIG. 6 is a partial sectioned view showing the detail of the optic fiber in its curved configuration.
Figure 7:
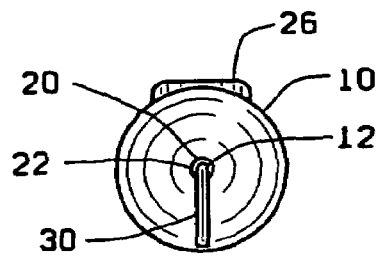
FIG. 7 is an end view of the instrument handle showing the optic fiber in its curved configuration.

A narrow tubular tip 30 constructed of a shape memory material, for example the metal alloy nitinol, extends through the center of the sleeve 20 and a portion of the handle bore 16. Alternatively, the tubular tip 30 could be constructed of other shape memory materials such as spring steel or plastics. The overall length of the tip 30 is slightly larger than the length of the sleeve 20. The tip 30 is positioned in the sleeve 20 and the handle center bore 16 so that a distal end 32 of the tip is positioned just inside the sleeve distal end 22 when the sleeve is moved to its forward most position shown in FIG. 4. The shape memory tip 30 passes through the slot 18 in the side of the handle and extends for a short distance through the center bore 16 behind the slot. As shown in FIG. 5, the tip proximal end 34 is secured stationary relative to the handle 10 by a set screw 36 that passes through the side of the handle and engages against the exterior of the tip 30. With the tip distal end 32 being positioned just inside the distal end 22 of the sleeve when the sleeve is moved to its pushed forward position, a distal end portion of the tip 30 projects from the sleeve distal end 22 when the finger pad 26 and the sleeve 20 are moved to their pulled back positions shown in FIG. 3. The distal end portion 38 of the shape memory tip 30 that projects from the sleeve distal end 22 is shown in FIG. 6. This distal end portion 38 of the tip is pre-bent as shown in FIG. 6 so that it will curve through an angle of 90° relative to the straight sleeve 20 when the sleeve is moved completely to its pulled back position as shown in FIG. 6. Other pre-bent angles of the tip greater than 90° or less than 90° may also be used.

To obtain the 90° bend when using nitinol as the shape memory material, the distal end portion 38 of the nitinol tip is bent in the configuration shown in FIG. 6 and is then heated to its annealing temperature (roughly 550° Celsius). Thus, when the finger pad 26 and the sleeve 20 are moved to their pulled back positions shown in FIGS. 3 and 6, the distal end portion 38 of the tip that projects from the distal end 22 of the sleeve gradually bends through 90° to its position shown in FIG. 6. By pushing the finger pad 26 and the sleeve 20 to their pushed forward position shown in FIG. 4, the distal end portion 38 of the tip is moved back into the interior of the sleeve 20 and the sleeve straightens out the bend in the tip distal end portion as it is moved to its position relative to the sleeve shown in FIG. 4.

To assist the sliding of the sleeve 20 over the distal end portion 38 of the tip, the interior of the sleeve is coated with a layer 40 of a sliding material such as Teflon®. The sliding material layer 40 extends only a short distance in the sleeve interior adjacent the sleeve distal end 22. The remainder of the sleeve interior is dimensioned slightly larger than the exterior diameter of the tubular tip 30 providing an air gap between the tip exterior and the sleeve interior. The layer of sliding material and the air gap both reduce actuation drag and enhance the ease of sliding the sleeve 20 over the exterior of the tip 30.

A length of optic fiber 42 extends between the handle 10 and a connector 44. The length of optic fiber 42 between the handle 10 and the connector 44 is protected by a layer of cladding as is conventional. The proximal end of the optic fiber enters the connector 44 and its cladding is removed. The exposed portion of optic fiber extends entirely through the connector 44 and its proximal end is positioned adjacent the end of the ferrule 46 projecting from the connector 44 as is conventional in optic fiber microsurgical instruments. The distal end of the optic fiber 42 enters the center bore 16 of the handle at the handle proximal end 14. Inside the handle center bore 16 the protective cladding of the optic fiber is removed and the optic fiber enters the proximal end 34 of the tubular tip 30. The exposed optic fiber extends entirely through the tip 30 to the distal end of the tip 32. In the preferred embodiment the distal end of the optic fiber extends past the tubular tip distal end 32 by 0.25 mm. With the optic fiber passing entirely through the shape memory tip 30, a distal end portion 48 of the optic fiber inside the tip distal end portion 38 is also bent through the 90° angle of the tip as the tip is bent through the 90° angle. Thus, when the finger pad 26 of the instrument is pushed forward, it extends the sleeve 20 to its pushed forward position in which the shape memory tip 30 and the distal end portion 48 of the optic fiber are completely contained inside the sleeve and are held in the straight configuration of the sleeve. When the finger pad 26 is moved to its pulled back position, the sleeve 20 is also moved back to its pulled back position causing the bent portion of the shape memory tip 30 and the distal end portion 48 of the optic fiber contained therein to be gradually exposed at the distal end of the sleeve. As the shape memory tip and the optic fiber are exposed at the end of the sleeve, they gradually bend from the initial straight configuration of the sleeve toward the 90° pre-bent configuration of the shape memory tip. In this manner, the optic fiber contained in the nitinol tip can be adjustably positioned through any angle between 0° when the shape memory tip and the optic fiber are entirely contained in the tubular sleeve at its pushed forward position, to a 90° bend when the shape memory tip and the optic fiber project from the sleeve distal end with the sleeve moved to its pulled back position.

In use of the first embodiment of the directional laser probe, the optic fiber connector 44 is first attached to a laser power source. With the finger pad 26 in its pushed forward position, the optic fiber is contained in the sleeve 20 which projects in a straight line from the distal end of the handle. The sleeve 20 is then inserted through a cannula positioned in an incision in the eye or inserted directly through the incision positioning the sleeve in the eye interior. The finger pad 26 is then slowly moved toward the rear of the handle causing the sleeve 20 to slowly move toward its pulled back position relative to the handle. This, in turn, causes the distal end portion 48 of the optic fiber contained in the pre-bent portion 38 of the shape memory tip to gradually bend from its straight configuration toward its 90° configuration. The bending of the fiber allows optimal positioning of the fiber tip to areas where a straight fiber may not reach. Rotation of the entire instrument about its center axis may be necessary to further direct the optic fiber tip. Once the proper location of the fiber tip is achieved, laser energy can then be delivered to the site of interest. Retraction of the tip is performed by first pushing the finger pad 26 forward causing the sleeve 20 to move toward its pushed forward position and causing straightening of the bent portion 48 of the optic fiber projecting from the sleeve. With the optic fiber contained in the sleeve, the sleeve is then pulled back through the surgical entry site.

In alternate embodiments of the invention the distal end 32 of the shape memory tip could be provided with a tool such as an extension pick 52 represented by dashed lines in FIG. 6. In addition, as set forth earlier, other shape memory materials could be used to construct the tip and the tip can be pre-bent to different angles. The sleeve 20 could also be mounted stationary relative to the handle 10 and the pre-bent tip 30 containing the optic fiber could be made moveable relative to the sleeve and handle to adjust the bend in the tip. Also, the sleeve 20 could be provided with a hole 54 for injection or suction of fluids through the hole 54 and the air gap created between the shape memory tip exterior surface and the sleeve interior surface behind the Teflon® layer 40. Furthermore, the actuation mechanism provided by the finger pad 26 can be replaced with other types of mechanisms that would produce the same axial movement of the sleeve 20, for example by a trigger mechanism manipulated by the surgeon's finger or by a squeeze mechanism that is squeezed by the surgeon's hand. In addition, a fiducial mark could be provided on the sleeve adjacent its distal end 22 to indicate to the surgeon which direction the distal end portion 38 of the tip will bend as it is extended out of the distal end 22 of the sleeve. This would be useful to the surgeon in accurately positioning the sleeve in the interior of the eye before the bending movement of the nitinol tip is commenced.

The above-described directional laser probe is intended for use as a disposable instrument. If the laser probe is to be reusable, the only difference in the construction is in the dimension of the optic fiber that passes through the instrument. The instrument can also be used as a steerable light source or as a directional laser probe depending upon the particular optic fiber inserted into the handle prior to use. To accommodate various light fiber sizes, the tubular shape memory tip 30 and the sleeve 20 could be increased to a larger diameter. An illumination optic fiber or a laser fiber would then be fed into the proximal end 14 of the handle and positioned in the tubular tip 30. A plug would be provided at the distal end 32 of the shape memory tip to securely fix the distal end of the optic fiber in the tip.

A second embodiment of the directional laser probe of the invention is shown in FIGS. 8 and 9. Like the first embodiment, the second probe embodiment is described herein as transmitting laser light for use in laser eye surgery. However, the probe is equally well suited for use in transmitting light for illumination in surgery. In addition, the probe can be designed as a disposable instrument or as a reusable instrument. Many of the component parts of the first described embodiment of the laser probe are employed in the second described embodiment shown in FIGS. 8 and 9. Therefore, for like component parts, the same reference numbers employed in the description of the first embodiment of the directional laser probe will be employed in the description of the second embodiment of the directional laser probe with the reference numbers being followed by a prime (').

The second embodiment of the directional laser probe shown in FIGS. 8 and 9 has an elongate narrow handle or hand piece 10' having opposite distal 12' and proximal 14' ends. The handle 10' is dimensioned to a size similar to that of a pencil to fit comfortably in the surgeons hand. The handle is preferably manufactured of a disposable medical grade plastic. A hollow bore 16' extends through the center of the handle from its distal end 12' to its proximal end 14'. The handle center bore 16' has a center axis that defines mutually perpendicular axial and radial directions relative to the handle 10'. The bore 16' has a necked down portion adjacent the handle distal end 12'. A recess 18' is formed radially into a side of the handle and intersects with the center bore 16'. The recess 18' extends axially along a short length of the handle forming an axial slot in the side of the handle.

A cylindrical, narrow rigid tube or sleeve 20' is received in the necked down portion of the handle bore 16' at the handle distal end 12'. The sleeve 20' is secured stationary to the handle 10' by adhesives or by other equivalent means. In the preferred embodiment of the invention the sleeve 20' is constructed of medical grade stainless steel. The sleeve 20' projects straight from the handle distal end 12' along the handle center bore axis to a distal end 22' of the sleeve. The opposite proximal end 24' of the sleeve is secured stationary in the necked down portion of the handle center bore 16'.

A length of optic fiber 60 having opposite proximal and distal 64 ends extends between the handle 10' and a connector 44'. The connection of the optic fiber proximal end to the connector 44' is the same as that of the previously described embodiment of the directional laser probe and therefore will not be described again here. The length of the optic fiber 60 between the handle 10' and the connector 44' is protected by a layer of cladding as is conventional. The optic fiber distal end 64 enters the handle center bore 16' at the handle proximal end 14'. Inside the handle center bore 16' the protective cladding of the optic fiber is removed exposing a portion of the length of the optic fiber 66. The exposed portion of the fiber 66 extends through the handle center bore 16', through the handle recess 18' and the sleeve 20' to the optic fiber distal end 64. The length of the optic fiber 60 in the handle interior bore 16' is dimensioned to easily slide through the bore.

The exposed portion 66 of the optic fiber adjacent the fiber distal end 64 is received in a narrow tubular tip 70 constructed of a shape memory material. In the preferred embodiment the shape memory material of the tubular tip 70 is a nitinol, however other types of materials may be used such as spring steel or plastic. The overall length of the tubular tip 70 between a proximal end 72 and a distal end 74 of the tip is larger than the length of the sleeve 20'. The exterior diameter dimension of the tubular tip 70 enables it to slide easily through the interior of the sleeve 20'. The tubular tip 70 is secured to the exposed portion 66 of the optic fiber 60 so that this portion of the optic fiber moves with the tubular tip 70 as the tip is reciprocated through the interior of the sleeve 20'. A distal end portion 76 of the tubular tip 70 is pre-bent so that it curves through an angle of 90° relative to the straight sleeve 20' when the distal end portion 76 of the tip is extended from the sleeve distal end 22' as shown in FIG. 8. Other pre-bent angles of the tip distal end portion 76 greater than 90°or less than 90° may also be employed.

A finger pad 80 is positioned in the handle recess slot 18' for axial sliding movement. The finger pad 80 is preferably constructed of a disposable medical grade plastic. The finger pad 80 can be manually moved through the recess between a pushed forward position of the finger pad 80 shown in FIG. 8 and a pulled back position of the finger pad 80 shown in FIG. 9. The finger pad 80 has an axially oriented hole 82 that receives the proximal end 72 of the shape memory tubular tip 70. The exposed portion of the optic fiber 66 that passes through the shape memory tubular tip 70 also passes through the axially oriented hole 82 of the finger pad 80. A set screw 84 is received in a complementary screw threaded hole in the top of the finger pad 80 and secures the finger pad to the proximal end 72 of the shape memory tubular tip 70. This also secures the finger pad 80 to the exposed portion 66 of the optic fiber received in the shape memory tubular tip 70. Thus, moving the finger pad 80 to its pushed forward position shown in FIG. 8 will also move the tubular tip 70 and the portion of the optic fiber 66 received in the tip to their forward most positions or pushed forward positions relative to the handle 10' and the sleeve 20'. With the finger pad 80 pushed to the forward end of the recess 18' the optic fiber distal end 64 is positioned at its greatest distance from the handle distal end 12' and the sleeve distal end 22' shown in FIG. 8. Moving the finger pad 80 to its pulled back position shown in FIG. 9 moves the shape memory tubular tip 70 and the portion of the optic fiber 66 received in the tubular tip to their pulled back positions relative to the handle 10' where the optic fiber distal end 74 projects its shortest distance from the handle distal end 12' and the sleeve distal end 22' shown in FIG. 9.

In using the second embodiment of the directional laser probe shown in FIGS. 8 and 9, the optic fiber connector 44' is first attached to a laser power source. With the finger pad 80 in its pulled back position in the handle recess 18', the exposed distal end portion 66 of the optic fiber and the shape memory tip 70 are contained in the sleeve 20' which projects in a straight line from the handle distal end 12'. The sleeve 20' is then inserted through a canula positioned in an incision in the eye or inserted directly through the incision positioning the sleeve distal end 22' in the eye interior. The finger pad 80 is then moved slowly through the handle recess 18' toward the handle distal end 12' which causes the optic fiber 60 to move through the handle interior bore 16', through the handle recess 18' and through the interior of the sleeve 20'. The portion 66 of the optic fiber contained in the shape memory tubular tip 70 gradually extends from the distal end 22' of the sleeve 20'. This causes the portion 66 of the optic fiber contained in the pre-bent portion 76 of the shape memory tubular tip to gradually bend from its straight configuration toward its 90° configuration. The bending of the optic fiber allows optimal positioning of the fiber distal end 64 to areas where a straight fiber may not reach. Rotation of the entire instrument about its center axis may be necessary to further direct the optic fiber tip. Once the proper location of the fiber tip is achieved, laser energy can then be delivered to the surgical site.

Retraction of the portion of the optic fiber 66 in the pre-bent portion 76 of the shape memory tubular tip is performed by moving the finger pad 80 through the handle recess 18' toward the handle proximal end 14'. This causes the portion of optic fiber 66 contained in the distal end portion 76 of the shape memory tubular tip 70 to be retracted into the sleeve 20' at the sleeve distal end 22' which causes the gradual straightening of the pre-bent portion 76 of the tubular tip. When the portion of the optic fiber 66 contained in the pre-bent portion 76 of the tubular tip is repositioned in the interior of the sleeve 20', the sleeve is then pulled back through the surgical entry site.

The alterations of the first embodiment of the directional laser probe described earlier can also be adapted to the second embodiment of the laser probe shown in FIGS. 8 and 9. In particular, the actuation mechanism provided by the finger pad 80 can be replaced with other types of mechanisms that would produce the same axial movement of the optic fiber and the distal end portion 76 of the shape memory tubular tip 70. For example, the finger pad 80 could be replaced by a trigger mechanism manipulated by the surgeon's finger, a squeeze mechanism that is squeezed by the surgeon's hand, a roller wheel or push down button, or a toggle lever. As in the first embodiment, the instrument of the second embodiment could also be used as a steerable light source instead of a directional laser probe.

While the present invention has been described by reference to specific embodiments, it should be understood that modifications and variations of the invention may be constructed without departing from the scope of the invention defined in the following claims.

What is claimed:

1. An ophthalmic surgery instrument comprising:
    an instrument handle;
    a single rigid tubular sleeve projecting from the instrument handle, the sleeve having a continuous exterior surface and a continuous interior surface that both extend along the sleeve from the instrument handle to a distal, terminal end of the sleeve, the sleeve being dimensioned for insertion of the sleeve distal, terminal end into an interior of an eye; and,
    an optic fiber extending through the handle and the sleeve, the optic fiber having a proximal end and an opposite distal end with a portion of the optic fiber at the optic fiber distal end having a bent configuration that is positioned in the sleeve and is held in a straight configuration by engagement with the sleeve interior surface, the optic fiber proximal end having a connector for connecting to a light source to transmit light through the optic fiber and project light from the optic fiber distal end, and the optic fiber distal end portion engaging in a sliding engagement with the sleeve interior surface and being extendable from the distal, terminal end of the sleeve to gradually bend from the straight configuration toward the bent configuration, the optic fiber distal end portion being dimensioned to bend to the bent configuration in an interior of an eye to project light from the optic fiber distal end in the interior of the eye and direct the light projected from the optic fiber distal end toward surgical sites lying in the interior of the eye.

2. The ophthalmic surgery instrument of claim 1, further comprising:
    the tubular sleeve being secured stationary to the handle.

3. The ophthalmic surgery instrument of claim 1, further comprising:
    the distal end portion of the optic fiber being constructed of a shape memory material.

4. The ophthalmic surgery instrument of claim 1, further comprising:
    the bent configuration of the optic fiber distal end portion being bendable to be straightened by sliding engagement of the optic fiber distal end portion with the sleeve interior surface when the optic fiber distal end portion is retracted into the sleeve interior surface.

5. The ophthalmic surgery instrument of claim 1, further comprising:
    the sleeve projecting straight from the handle.

6. The ophthalmic surgery instrument of claim 1, further comprising:
    the optic fiber being the only optic fiber that extends through the handle and the sleeve.

7. The ophthalmic surgery instrument of claim 1, further comprising:
    the instrument being a laser probe.

8. The ophthalmic surgery instrument of claim 1, further comprising:
    a mechanism on the handle and connected to the optic fiber to selectively move the optic fiber between a pushed forward position of the optic fiber where the optic fiber distal end portion is extended from the sleeve distal, terminal end, and a pulled back position of the optic fiber where the optic fiber distal end portion is retracted into the interior surface of the sleeve.

9. The ophthalmic surgery instrument of claim 1, further comprising:
    the optic fiber having an exposed distal end surface opposite the optic fiber proximal end.

10. The ophthalmic surgery instrument of claim 1, further comprising:
    the sleeve being constructed of surgical steel.

11. An ophthalmic surgery instrument comprising:
    an elongate, narrow handle having opposite proximal and distal ends and a hollow bore extending through the handle;
    an elongate, narrow rigid tubular sleeve having opposite proximal and distal ends with the sleeve proximal end being fixed stationary to the handle distal end, the sleeve having a continuous exterior surface and a continuous interior surface that extend between the sleeve proximal and distal ends with the sleeve interior surface defining an interior bore of the sleeve that communicates with the handle interior bore at the proximal end of the sleeve and ends at the sleeve distal end, the sleeve distal end being dimensioned for insertion of the sleeve distal end into an interior of an eye;
    an optic fiber having a length that extends between opposite proximal and distal ends of the optic fiber, the optic fiber proximal end having a connector for connecting to a light source to transmit light through the optic fiber and project light from the optic fiber distal end, the optic fiber length extending through the handle interior bore and the sleeve interior bore for relative movement of the optic fiber relative to the handle and sleeve, and the optic fiber extending to an exposed distal end surface of the optic fiber with a distal end portion of the optic fiber length adjacent the optic fiber distal end surface having a bent configuration that engages in sliding engagement with the sleeve interior surface and is extendable from the sleeve distal end to cause the optic fiber distal end portion to gradually bend toward the bent configuration, the optic fiber distal end portion being dimensioned to bend to the bent configuration in an interior of an eye to project light from the optic fiber distal end in the interior of the eye and direct the light projected from the optic fiber distal end toward surgical sites lying in the interior of the eye.

12. The ophthalmic surgery instrument of claim 11, further comprising:
the optic fiber distal end portion engaging against the interior surface of the sleeve to straighten the bent configuration of the optic fiber distal end portion.

13. The ophthalmic surgery instrument of claim 11, further comprising:
the optic fiber being the only optic fiber that extends through the interior bore of the handle and the interior bore of the sleeve.

14. The ophthalmic surgery instrument of claim 11, further comprising:
the sleeve being constructed of surgical steel.

15. The ophthalmic surgery instrument of claim 11, wherein:
the instrument is an illuminating probe.

16. The ophthalmic surgery instrument of claim 11, further comprising:
the distal end portion of the optic fiber being contained in a tubular tip constructed of a shape memory material.

17. The ophthalmic surgery instrument of claim 11, further comprising:
the sleeve projecting along a straight line from the handle for the entire length of the sleeve.

18. The ophthalmic surgery instrument of claim 11, further comprising:
the instrument being a laser probe.

19. The ophthalmic surgery instrument of claim 11, further comprising:
the optic fiber having an exposed distal end surface opposite the optic fiber proximal end.

20. The ophthalmic surgery instrument of claim 11, further comprising:
a mechanism on the handle and connected to the optic fiber to selectively move the optic fiber between a pushed forward position of the optic fiber where the optic fiber distal end portion is extended from the sleeve distal, terminal end, and a pulled back position of the optic fiber where the optic fiber distal end portion is retracted into the interior surface of the sleeve.

21. The ophthalmic surgery instrument of claim 11, further comprising:
the sleeve having continuous exterior and interior surfaces that extend for an entire length of the sleeve projecting from the handle distal end.

22. An ophthalmic surgery instrument comprising:
an elongate, narrow handle having opposite proximal and distal ends and a hollow interior bore extending through the handle;
a single, elongate, narrow rigid tubular sleeve having a length with opposite proximal and distal ends, the sleeve proximal end being fixed stationary to the handle distal end, the sleeve having continuous exterior and interior surfaces that extend for the entire length of the sleeve, the sleeve interior surface defining an interior bore of the sleeve that communicates with the handle interior bore, the sleeve distal end being dimensioned for insertion of the sleeve distal end into an interior of an eye;
a single optic fiber having a length that extends between opposite proximal and distal ends of the optic fiber, the optic fiber proximal end having a connector for connecting to a separate light source to transmit light through the optic fiber and project light from the optic fiber distal end, the optic fiber distal end having an exposed end surface, the optic fiber length extending through the handle interior bore and through the sleeve interior bore for relative movement of the optic fiber relative to the handle and the sleeve, the optic fiber having a distal end portion adjacent the distal end surface of the optic fiber with the distal end portion having a bent configuration that engages in sliding engagement with the sleeve interior surface and is extendable from the sleeve distal end in response to movement of the optic fiber in the sleeve interior bore to cause the optic fiber distal end portion to gradually bend toward the bent configuration as the distal end portion is extended from the sleeve distal end, the optic fiber distal end portion being dimensioned to bend to the bent configuration in an interior of an eye to project light from the optic fiber distal end in the interior of the eye toward surgical sites lying in the interior of the eye.

23. The ophthalmic surgery instrument of claim 22, further comprising:
the sleeve being constructed entirely of surgical steel.

24. The ophthalmic surgery instrument of claim 22, further comprising:
the sleeve projecting along a straight line from the handle for the entire length of the sleeve.

25. The ophthalmic surgery instrument of claim 22, further comprising:
the distal end portion of the optic fiber being constructed of a shape memory material.

26. The ophthalmic instrument of claim 22, further comprising:
the optic fiber being the only optic fiber that extends through the handle and the sleeve.

* * * * *